United States Patent
Winkelhake et al.

(10) Patent No.: US 7,958,986 B2
(45) Date of Patent: Jun. 14, 2011

(54) PASSENGER CONVEYOR HANDRAIL DRIVE DEVICE

(75) Inventors: Dirk Winkelhake, Bolton, CT (US); Raymond J. Moncini, Southington, CT (US)

(73) Assignee: Otis Elevator Company, Farmington, CT (US)

( * ) Notice: Subject to any disclaimer, the term of this patent is extended or adjusted under 35 U.S.C. 154(b) by 25 days.

(21) Appl. No.: 12/514,147

(22) PCT Filed: Dec. 21, 2006

(86) PCT No.: PCT/US2006/062468
§ 371 (c)(1),
(2), (4) Date: May 8, 2009

(87) PCT Pub. No.: WO2008/076134
PCT Pub. Date: Jun. 26, 2008

(65) Prior Publication Data
US 2010/0025185 A1    Feb. 4, 2010

(51) Int. Cl.
*B66B 21/00* (2006.01)

(52) U.S. Cl. .................... 198/331; 198/330

(58) Field of Classification Search ............ 198/322, 198/330, 331
See application file for complete search history.

(56) References Cited

U.S. PATENT DOCUMENTS

| | | | |
|---|---|---|---|
| 2,221,403 A * | 11/1940 | Lindquist et al. ............ 198/331 |
| 3,658,166 A | 4/1972 | Hara et al. | |
| 4,580,675 A | 4/1986 | Boltrek | |
| 5,072,820 A | 12/1991 | Steffen et al. | |
| 5,090,551 A * | 2/1992 | Yasuhara et al. ............ 198/323 |
| 5,092,446 A * | 3/1992 | Sullivan et al. ............. 198/323 |
| 5,295,567 A | 3/1994 | Zaharia et al. | |
| 5,842,554 A | 12/1998 | Stoxen et al. | |
| 6,161,674 A | 12/2000 | Aulanko et al. | |
| 6,267,219 B1 | 7/2001 | Spannhake et al. | |
| 6,971,497 B2 * | 12/2005 | Illedits et al. ............... 198/330 |
| 2006/0070846 A1 | 4/2006 | Andreas et al. | |

FOREIGN PATENT DOCUMENTS

| | | |
|---|---|---|
| DE | 19539796 A1 | 4/1997 |
| EP | 0883568 B1 | 10/2002 |
| JP | 2000053353 | 2/2000 |

(Continued)

OTHER PUBLICATIONS

International Search Report and Written Opinion of the International Searching Authority for International application No. PCT/US2006/062468 mailed Sep. 13, 2007.

(Continued)

*Primary Examiner* — James R Bidwell
(74) *Attorney, Agent, or Firm* — Carlson, Gaskey & Olds PC

(57) ABSTRACT

An exemplary device for driving a handrail of a passenger conveyor includes a handrail drive member configured to engage a handrail. A motor is associated with the drive member such that a driving output of the motor is exclusively for moving the handrail drive member. An exemplary passenger conveyor includes a step chain and a handrail. A step chain motor is associated with the step chain for moving the step chain. A handrail motor that is distinct from the step chain motor is associated with the handrail for moving the handrail.

11 Claims, 2 Drawing Sheets

FOREIGN PATENT DOCUMENTS

| | | |
|---|---|---|
| JP | 2001139271 | 5/2001 |
| JP | 2001220083 | 8/2001 |
| WO | 0010902 | 3/2000 |
| WO | 03066500 A1 | 8/2003 |
| WO | 2004035451 A2 | 4/2004 |
| WO | 2005097650 A2 | 10/2005 |

OTHER PUBLICATIONS

International Preliminary Report on Patentability for International application No. PCT/US2006/062468 mailed Apr. 8, 2009.

* cited by examiner

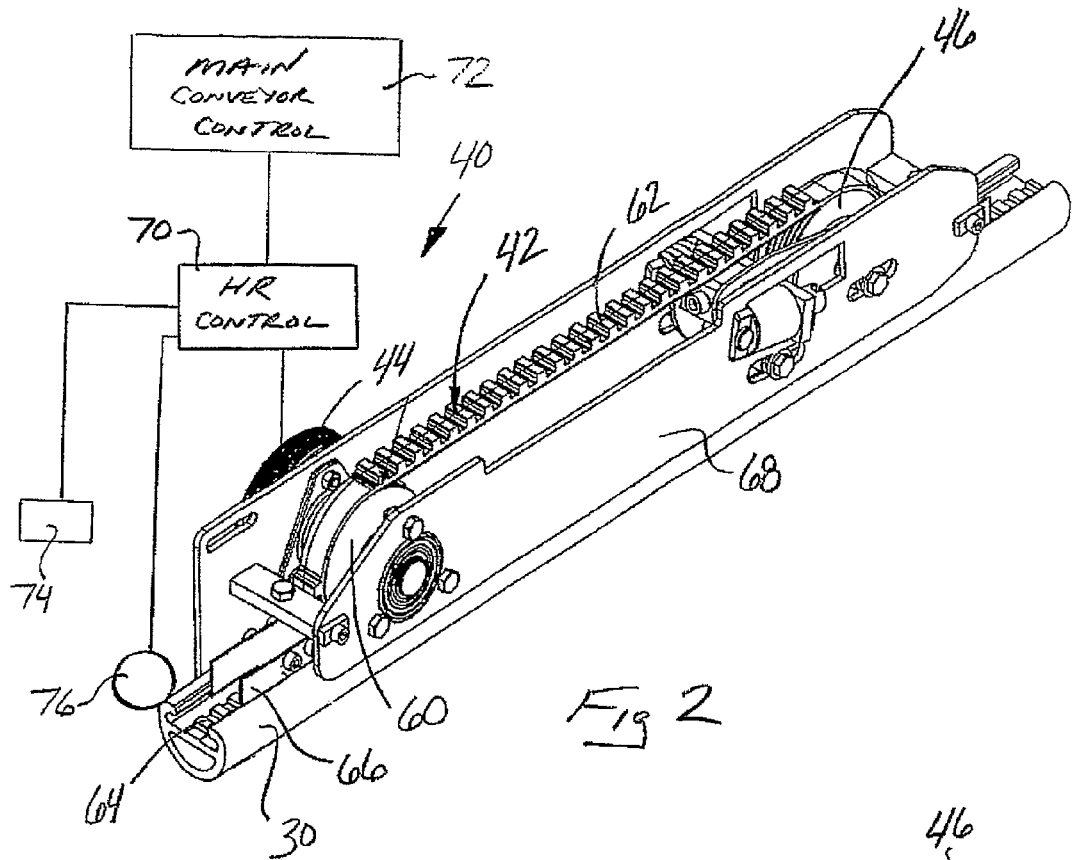
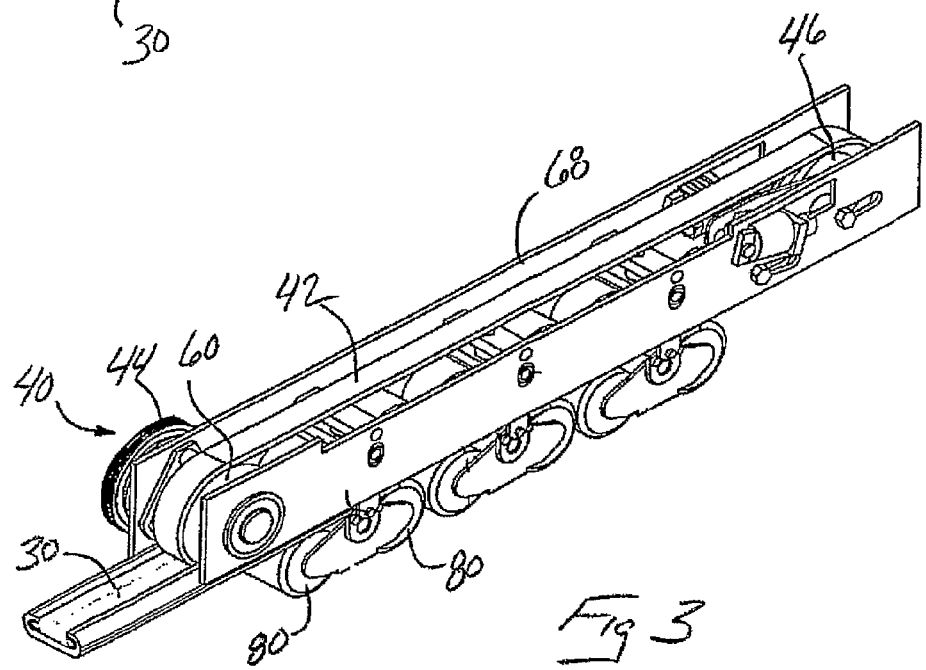

PASSENGER CONVEYOR HANDRAIL DRIVE DEVICE

BACKGROUND

Passenger conveyors have proven effective for carrying people between different levels within a building or across an elongated pathway, for example. Typical arrangements include a plurality of steps or a belt upon which an individual stands to be carried from one location to another. A handrail typically rides over a balustrade and provides a surface for an individual to grab onto while riding on the conveyor. Typical handrail configurations have a generally flat surface oriented parallel to the ground or the direction of movement of the conveyor (e.g., on an angle relative to vertical along the rise of an escalator).

Handrails are driven to move in unison with the steps or moving belt. A handrail drive mechanism causes the desired movement of the handrail. Typical arrangements link a motor responsible for driving the step chain to the handrail drive system. The same motor drives the stop chain and the handrail to ensure that the two move in unison. While such arrangements have proven useful, those skilled in the art are always striving to make improvements. One example improvement is shown in the published United States Patent Application 2006/0070846.

For example, it would be useful to simplify the installation and maintenance procedures associated with passenger conveyors. The interconnection between the step chain and handrail drive systems contributes to the complexity and time-consuming nature of such processes. The handrail drive system is also believed to be a major contributor to maintenance and repair requests and it would be useful to provide an improved arrangement to minimize the times a conveyor is unavailable for passenger use.

SUMMARY

An exemplary passenger conveyor handrail drive device includes a drive member configured to engage a handrail. A motor is associated with the drive member such that a driving force output from the motor is exclusively for propelling the drive member.

An exemplary passenger conveyor includes a step chain and a handrail. A step chain motor is associated with the step chain for moving the step chain. A handrail motor that is distinct from the step chain motor is associated with the handrail for moving the handrail.

An exemplary method of installing a handrail drive system includes positioning a handrail drive member relative to a handrail for transmitting a driving force from the drive member to the handrail and coupling the handrail drive member with a motor that is distinct from a motor used to drive a step chain of the corresponding passenger conveyor.

The various features and advantages of the disclosed examples will become apparent to those skilled in the art from the following detailed description. The drawings that accompany the detailed description can be briefly described as follows.

BRIEF DESCRIPTION OF THE DRAWINGS

FIG. 2 schematically shows an example drive device.

FIG. 3 schematically shows selected portions of another example drive device.

DETAILED DESCRIPTION

Figure 1:
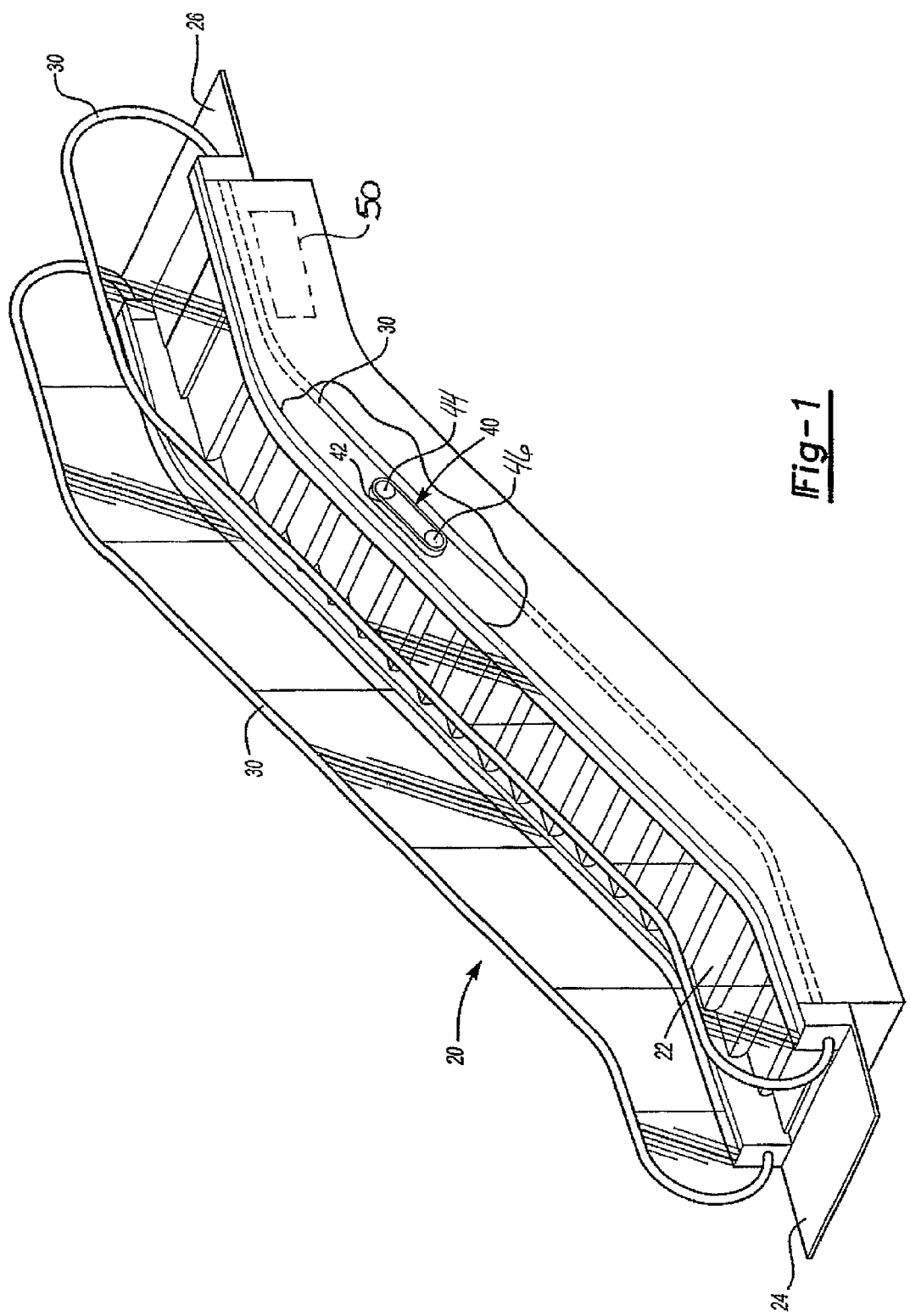
FIG. 1 schematically shows selected portions of an example passenger conveyor including a handrail driving device designed according to an embodiment of this invention.

FIG. 1 schematically shows a passenger conveyor 20. In this example, the passenger conveyor is an escalator having a plurality of steps 22 for carrying passengers between landings 24 and 26 at different levels within a building. This invention is not limited to escalators but is also applicable to other forms of passenger conveyors such as moving walkways, for example.

The example passenger conveyor of FIG. 1 includes a handrail 30 that moves along with the steps 22. A handrail drive device 40 includes a drive member 42 that engages the handrail 30 to propel the handrail 30 in a desired direction. The example handrail drive device 40 includes a motor 44 that is dedicated to moving the handrail 30. The motor 42 is associated with a wheel at one end of a loop followed by the drive member 42, which comprises a belt in this example. Another wheel 46 is at an opposite end of the loop. The motor 44 causes the drive member 42 to rotate about the loop, which drives the handrail 30 as desired because of engagement between the handrail 30 and the drive member 42.

The handrail drive device 40 is distinct from a drive assembly 50 used to propel the steps 22 by driving a step chain (not illustrated). The motor 44 is distinct from a motor of the drive assembly 50. Accordingly, the illustrated arrangement is different than traditional passenger conveyor systems where the handrail was driven by the same motor used to move the step chain.

FIG. 2 schematically shows one example handrail drive device 40. In this example, the motor 44 comprises a permanent magnet motor. One advantage to using a permanent motor is that relatively large torques required to drive a handrail can be achieved with a relatively small sized motor. Another advantage of a permanent magnet motor is that it allows for closely controlling the speed at which the motor 44 moves the drive member 42.

This example drive member 42 comprises a toothed belt that follows a loop around the wheel 46 and a wheel 60 that can be considered a drive sheave because it is driven by the motor 44. The toothed belt drive member 42 has teeth 62 that are configured to engage correspondingly configured teeth 64 on the handrail 30. A guiding support 66 maintains the corresponding portion of the handrail 30 in a position to ensure desired engagement between the teeth 62 and 64. As the motor 44 rotates the wheel 60, the drive member 42 moves and causes a desired movement of the handrail 30. A mounting structure 68 facilitates securing the device 40 in a desired position on a conveyor truss or other support structure.

The illustrated example includes a handrail drive controller 70 that controls operation of the motor 44 to ensure that the handrail is moving when needed and at a desired speed that is coordinated with movement of the steps 22. The handrail drive controller 70 communicates with a main conveyor controller 72, which is responsible for controlling the drive assembly 50. The main conveyor controller 72 provides information to the handrail drive controller 70 regarding the speed and direction of movement of the steps 22 so that the handrail drive controller 70 can control the motor 44 to achieve a corresponding handrail movement.

In one example a connection between the main conveyor controller 72 and the handrail drive controller 70 operates as a power supply to the handrail drive device 40. For example, whenever the main conveyor controller 72 determines that the conveyor is stopped or out of service, it controls whether power is supplied to the handrail drive device according to preset criteria.

The example handrail drive controller 70 also receives information from a step chain sensor 74 that indicates a speed of movement of the step chain and the steps 22. One example includes at least one proximity sensor arranged to detect movement of pins associated with rollers of the steps or step chain to provide an indication of a speed of movement. A handrail speed sensor 76 provides an indication of actual handrail speed. Given this description, those skilled in the art will be able to select from commercially available sensors to realize an arrangement that meets their particular needs. The handrail drive controller 70 uses such sensor information and knowledge regarding the operating characteristics of the motor 44 to customize the operation of the motor 44 to ensure that the handrail 30 is moving at a speed that is appropriate for a current speed of step movement. In one example, the handrail drive controller 70 comprises a variable frequency controller, which allows for customizable speed control of the motor 44.

Those skilled in the art who have the benefit of this description will be able to program a controller to perform in a manner that meets the requirements of their particular installation.

FIG. 3 shows another example handrail drive device. In this example, the drive member 42 and the handrail 30 are configured differently compared to the example of FIG. 2. In this example, the more traditional flat drive belt and handrail configurations are used. The flat belt drive member 42 in this example relies upon a frictional engagement with the handrail 30. Rollers 80 engage one side of the handrail to ensure a proper driving engagement between the handrail 30 and the drive member 42. Otherwise, the example of FIG. 3 operates like the example of FIG. 2.

One advantage associated with the disclosed examples is that the handrail drive device 40 can be located anywhere within a passenger conveyor system that is convenient for an installer provided that the structure 68 can be adequately supported in a position to provide proper engagement between the drive member 42 and the handrail 30. This not only simplifies installation but provides advantages for maintenance or repair as the handrail drive device can be located more conveniently. When the handrail drive device is located remotely from the step chain drive assembly, each drive can be serviced without any interference from the other.

Another advantage is that a handrail drive device 40 can be retrofit into an existing conveyor system. The coupling between the step chain drive and the handrail drive can be disconnected or otherwise disabled and the handrail drive device 40 can be inserted in its place. This allows for a wider range of choice in replacement handrails, for example, as different handrail configurations can be accommodated by a correspondingly configured handrail drive device 40. For example, it may be possible to insert a positive drive handrail (having drive teeth) in place of a friction-based driven handrail by introducing a handrail drive device 40 as shown in FIG. 2. Such a change is not possible with a conventional arrangement that is configured for only one type of handrail.

Another advantage associated with the disclosed examples is that the handrail operation is smoother compared to an arrangement where the handrail is driven by the same motor used to drive the step chain. The dedicated motor of the example devices provides a smoother transmission of driving force to the handrail and avoids the vibrations associated with some movements of a step chain.

Additionally, separating the handrail drive motor from a step chain motor reduces the complexity of each drive arrangement, facilitates less maintenance and reduces the likelihood of a need for repair.

The preceding description is exemplary rather than limiting in nature. Variations and modifications to the disclosed examples may become apparent to those skilled in the art that do not necessarily depart from the essence of this invention. The scope of legal protection given to this invention can only be determined by studying the following claims.

We claim:

1. A device for driving a handrail of a passenger conveyor, comprising:
   a handrail drive member configured to engage a handrail;
   a motor associated with the drive member such that a driving output of the motor is exclusively for moving the handrail drive member;
   a handrail controller coupled with the motor for controlling operation of the motor to ensure that an associated handrail moves at a desired speed;
   a handrail speed sensor that provides an indication of a speed of the associated handrail to the handrail controller; and
   a step chain speed sensor that provides an indication of a speed of an associated step chain to the handrail controller; and
   wherein the handrail controller controls operation of the motor responsive to at least one of the sensor indications and the handrail controller is connected with a main controller of an associated passenger conveyor, a connection between the main controller and the handrail controller comprising a power supply to the device, the main controller being configured to determine when to supply power to at least the motor through the power supply.

2. The device of claim 1, wherein the handrail controller comprises a variable frequency controller.

3. The device of claim 1, wherein the motor comprises a permanent magnet motor.

4. The device of claim 1, wherein the drive member comprises a belt that has a surface arranged to engage a surface on the handrail for moving the handrail.

5. The device of claim 1, wherein the main controller is configured to determine when to supply power to the handrail controller on the power supply.

6. A passenger conveyor system, comprising:
   a step chain;
   a handrail;
   a step chain motor associated with the step chain for moving the step chain; and
   a handrail drive motor that is distinct from the step chain motor and is associated with the handrail for moving the handrail;
   a main conveyor controller that controls the step chain motor; and
   a handrail drive controller that controls the handrail drive motor, wherein the handrail drive controller communicates with the main conveyor controller and responsively controls the handrail drive motor, a connection between the main conveyor controller and the handrail drive controller comprising a power supply for supplying power to at least the handrail drive motor, the main conveyor controller being configured to determine when to supply power to the handrail drive motor.

7. The system of claim 6, comprising
   a handrail speed sensor that provides an indication of a speed of the handrail to the handrail drive controller; and a step chain speed sensor that provides an indication of a speed of the step chain to the handrail drive controller; and wherein the handrail drive controller controls operation of the handrail drive motor responsive to at least one of the sensor indications.

8. The system of claim 6, wherein the handrail drive controller comprises a variable frequency controller.

9. The system of claim 6, wherein the handrail drive motor comprises a permanent magnet motor.

10. The system of claim 6, comprising a drive member for moving the handrail responsive to operation of the handrail drive motor, wherein the drive member comprises a belt having a surface arranged to engage a surface on the handrail for moving the handrail.

11. The system of claim 6, wherein the main conveyor controller is configured to determine when to supply power to the handrail drive controller on the power supply.

* * * * *